(12) United States Patent
Aducci et al.

(10) Patent No.: US 7,932,233 B2
(45) Date of Patent: Apr. 26, 2011

(54) FUNGAL PHYTOTOXIN FUSICOCCIN FOR THE TREATMENT AND DIAGNOSIS OF COAGULATION-CORRELATED PATHOLOGIES

(75) Inventors: Patrizia Aducci, Rome (IT); Lorenzo Camoni, Rome (IT); Cristina Di Lucente, Rome (IT); Sabina Visconti, Rome (IT)

(73) Assignee: Universita'Degli Studi Roma "Tor Vergata", Rome (IT)

( * ) Notice: Subject to any disclaimer, the term of this patent is extended or adjusted under 35 U.S.C. 154(b) by 313 days.

(21) Appl. No.: 12/126,205

(22) Filed: May 23, 2008

(65) Prior Publication Data

US 2009/0291905 A1    Nov. 26, 2009

(51) Int. Cl.
*A01N 43/04* (2006.01)
*A61K 31/70* (2006.01)

(52) U.S. Cl. .............................. 514/25; 514/26
(58) Field of Classification Search .................. None
See application file for complete search history.

(56) References Cited

OTHER PUBLICATIONS

Biophysical Research Communications (1997), vol. 238, pp. 758-763.*

* cited by examiner

*Primary Examiner* — Patrick T Lewis
(74) *Attorney, Agent, or Firm* — Arent Fox LLP

(57) ABSTRACT

The present invention concerns the use of tricyclic terpenes chosen from the group consisting of fusicoccin, ophyobolins or cotylenins for the therapy and diagnosis of coagulation-correlated pathologies such as Bernard-Soulier syndrome (BSS), von Willebrand disease (vWD), Glanzmann's thrombasthenia or thrombocytopenia.

5 Claims, 6 Drawing Sheets

Figure 1:
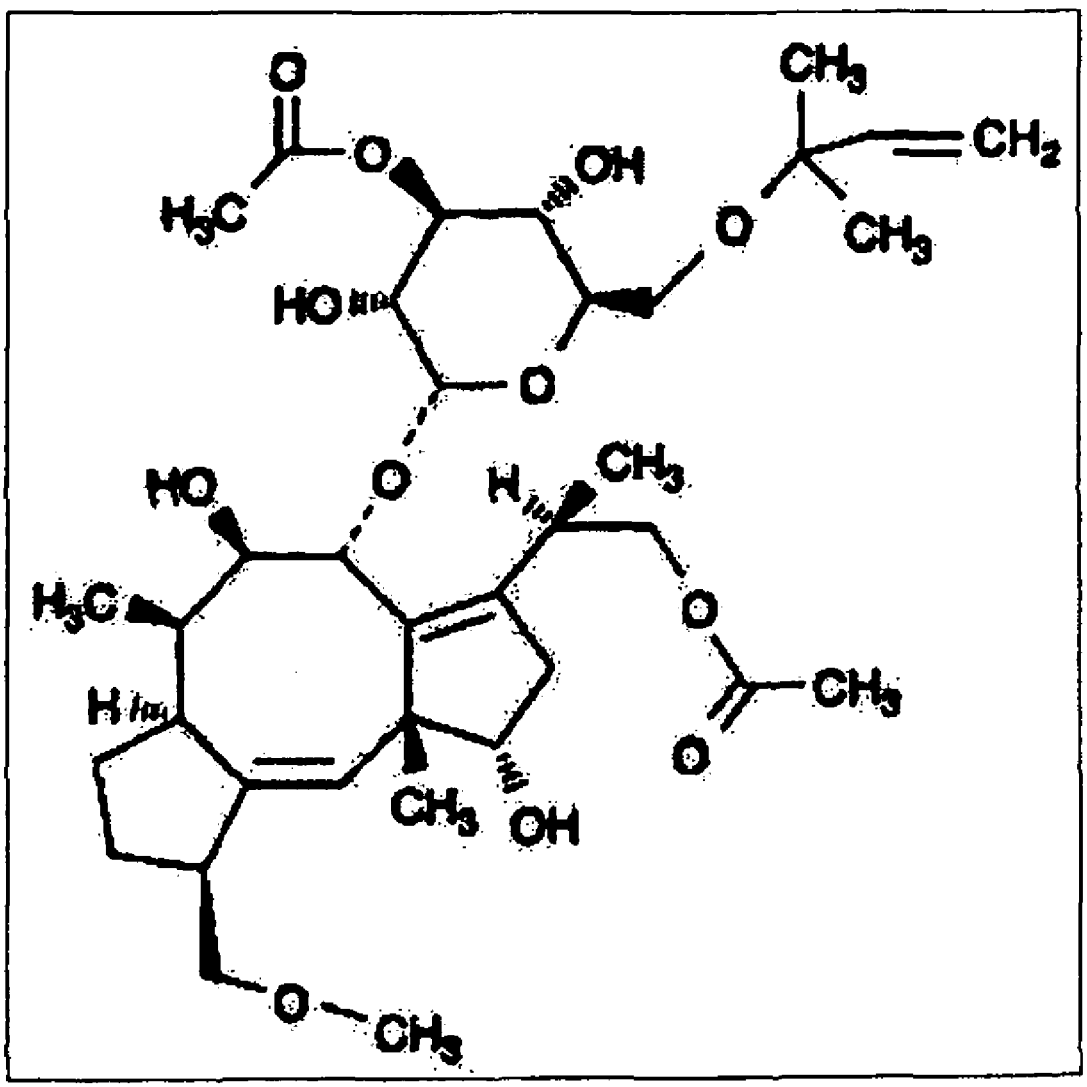

FUNGAL PHYTOTOXIN FUSICOCCIN FOR THE TREATMENT AND DIAGNOSIS OF COAGULATION-CORRELATED PATHOLOGIES

The present invention concerns the use of the fungal phytotoxin fusicoccin for the treatment and diagnosis of coagulation-correlated pathologies.

Hemostasis is a complex process which changes blood from a fluid to a solid state. Intact blood vessels are central to moderating blood's tendency to clot, but because of injury to vessels hemostasis ensues (Furie, 1988).

Platelet adhesion and aggregation play important roles in thrombosis and hemostasis. In fact, at sites of high shear stress, such as in smaller vessels or stenosed arteries (Ware, 1998), platelets become activated by a combination of exposed extracellular matrix proteins. The glycoprotein Ib-IX-V (GPIb-IX-V) complex, expressed by the platelets, has a critical function in these processes by acting as the primary receptor for the von Willebrand Factor (vWF). Interaction of the GPIbα chain of GPIb-IX-V with matrix-bound multimeric vWF mediates platelet activation, triggering to $\alpha_{11B}\beta_3$ integrins activation and consequent platelet spreading and aggregation (Gralnick et al., 1985).

In the last years the involvement of regulatory 14-3-3 proteins in the regulation of GPIbα function has emerged. 14-3-3 proteins are a family of highly conserved proteins with molecular mass of 30 kDa, expressed in all eukaryotic organisms. They exist in a number of isoforms and form homo- and heterodimers. 14-3-3s play a central role in the regulation of many cellular processes, such as cell cycle, differentiation, apoptosis, and mitogenic signal transduction (Fu et al., 2000). The common feature of 14-3-3s is their ability to bind phosphorylated consensus motifs on target proteins (Muslin et al., 1996; Yaffe et al., 1997); this accounts for their diverse regulatory functions.

Most of the characterized 14-3-3 interactions are mediated by two canonical internal binding motifs, mode I (RSXpSXP, where X is any amino acid and pS is phosphoserine) and mode II (RXΦXpSXP, where Φ is an aromatic or aliphatic amino acid).

Two 14-3-3 binding sites have been identified in GPIb-IX. The first has been identified in GPIbβ and presents a canonical binding motif characterized by RLpS$^{166}$LTDP sequence (Andrews at al., 1998). The second has been identified at the C terminal end of the Ibα subunit and it is constituted by the SGHpS$^{609}$L motif (Du et al., 1996).

Recently, the evidence that 14-3-3s play a critical role in regulating vWF binding function of GPIb-IX-V and vWF-mediated platelet adhesion was provided (Dai et al., 2005).

Among the coagulation-correlated pathologies, Bernard-Soulier syndrome (BSS) and von Willebrand disease (vWD) are common hereditary coagulation abnormalities described in humans. They arise from a qualitative or quantitative deficiency of GPIbα or vWF, respectively (Pham and Wang, 2007; Sadler, 1994). Glanzmann's thrombasthenia, is a blood disorder in which platelets are defective in $\alpha_{IIB}\beta_2$ integrin (Seligsohn, 2002). Furthermore, a large number of bleeding pathologies lead to increased destruction or decreased production of platelets, hence resulting in thrombocytopenia (Kaushansky, 2008).

The therapy for Von Willebrand disease consists in different approaches. Desmopressin (DDAVP) is a synthetic hormone that can be usually taken by injection or nasal spray. It makes human body release more von Willebrand factor and factor VIII into the bloodstream. DDAVP works for most patients who have type 1 VWD and for some who have type 2 VWD. Von Willebrand factor replacement therapy is an infusion of a concentrate of von Willebrand factor and factor VIII into a vein in the arm. Antifibrinolytic drugs help prevent the breakdown of blood clots. They're mostly used to stop bleeding after minor surgery, tooth extraction, or an injury. They may be used alone or together with DDAVP and replacement therapy. Fibrin glue is medicine that's placed directly on a wound to stop the bleeding.

The treatment with DDAVP can cause some side effects that include local injection site reactions, facial flushing, headache and changes in blood pressure.

As far as Bernard Soulier syndrome is concerned, specific treatment of bleeding episodes includes the following: antifibrinolytic agents, such as epsilon aminocaproic acid, may be useful for mucosal bleeding. For surgery or life-threatening hemorrhage, platelet transfusion is the only available therapy. Platelet transfusions should be reserved for surgery or potentially life-threatening bleeding. The patient may develop antiplatelet antibodies because of glycoproteins Ib/IX/V, which are present on the transfused platelets but absent from the patient's own platelets. Desmopressin acetate (DDAVP) has been shown to shorten the bleeding time in some, but not all, patients with Bernard-Soulier syndrome (BSS). DDAVP may be useful for minor bleeding episodes. Recently, recombinant activated factor VII has been used in patients with congenital platelet disorders, including BSS.

As far as therapy for Glanzmann's thrombasthenia is concerned, platelet transfusions have been the mainstay of treatment for bleeding episodes. However, patients may develop antibodies to transfused platelets making future transfusions ineffective.

In the light of the above it would be desiderable to have at disposal new drugs promoting platelet aggregation able to overcome the disadvantages of already known therapies.

Fusicoccin (FC) is a phytotoxic metabolite produced by the fungus *Fusicoccum(Phomopsis) amygdali*, the causative agent of peach and almond canker (Aducci et al., 2003). FC is the α-glucoside of a carbotricyclic diterpene, whose basic ring structure is found in other natural products, such as ophyobolins and cotilenins (Aducci et al., 2003). FC toxicity interferes with a number of physiological and biochemical processes of higher plants (Graniti et al., 1994). FC effects are due to the ability of the phytotoxin to irreversible activate the plasma membrane H*-ATPase (Marrè, 1979). FC stimulates the association of 14-3-3 proteins to the C-terminal autoinhibitory domain of the proton pump, thereby leading to its displacement and consequently to H$^+$-ATPase activation. The H$^+$-ATPase binding site for 14-3-3 proteins is generated upon phosphorylation of a conserved threonine residue within the C terminal sequence YTV (Aducci et al., 2002). This characteristic binding site has been therefore proposed as mode III (Coblitz et al., 2006). It is also known that FC is uneffective in the interaction between 14-3-3 and targets with canonical binding sites (Aducci et al., 2002).

The Authors of the present invention have now found that fusicoccin stimulates the binding of 14-3-3 proteins to the platelet protein Glycoprotein Ibα, which also contains a mode III 14-3-3 binding sequence. Glycoprotein Ibα is the platelet receptor for von Willebrand Factor and it is essential in the first step of the coagulation process. Fusicoccin binding promotes activation of Glycoprotein Ibα and consequent adhesion of platelets to von Willebrand Factor, therefore triggering the aggregation process. Therefore, these data propose fusicoccin as a novel compound able to induce platelet aggregation. Particularly, the inventors have now found that fusicoccin induces a mild and dose-dependent platelet aggregation that renders this phytotoxin advantageously suitable for diagnosis and therapy of bleeding disorders such as Bernard-Soulier syndrome (BSS), von Willebrand disease (vWD), Glanzmann's thrombasthenia, thrombocytopenia.

In fact, diagnosis for these pathologies is currently made by measuring the ability of platelets to respond to exogenous modulators, such as ristocetin (De Luca et al., 2000) and botrocetin (Marsh, 2001). The bacterial glycopeptide ristocetin and the snake venom toxin botrocetin modulate vWF to elicit platelet glycoprotein Ib binding activity and lead to platelet agglutination (De Luca et al., 2000; Marsh, 2001). However, PRP from patients affected by BSS or vWD shows an abnormal response to these molecules. Therefore, the dramatic effects on platelet aggregation induced by ristocetin and botrocetin made them unsuitable for therapy. On the contrary, FC induces a mild platelet aggregation by a different molecular mechanism in a dose-dependent manner. This renders feasible the use of FC in diagnosis and therapy of bleeding disorders.

It is therefore an object of the present invention a pharmaceutical composition comprising as active ingredient a therapeutically effective amount of at least one tricyclic terpenes chosen from the group consisting of fusicoccin, ophyobolins or cotylenins, in association with one or more pharmaceutically acceptable diluents, excipients and/or inert carriers. The pharmaceutical composition according to the present invention can be used for the treatment of coagulation-correlated pathologies, such as Bernard-Soulier syndrome (BSS), von Willebrand disease (vWD), Glanzmann's thrombasthenia or thrombocytopenia.

It is further object of the present invention a method for treating coagulation-correlated pathologies comprising administering a therapeutically effective amount of at least one tricyclic terpenes chosen from the group consisting of fusicoccin, ophyobolins or cotylenins to a subject in need of such treatment. As mentioned above, the coagulation-correlated pathologies are chosen from the group consisting of Bernard-Soulier syndrome (BSS), von Willebrand disease (vWD), Glanzmann's thrombasthenia or thrombocytopenia.

It is an object of the present invention also a method of using at least one tricyclic terpenes chosen from the group consisting of fusicoccin, ophyobolins or cotylenins for in vitro diagnosing of coagulation-correlated pathologies, such Bernard-Soulier syndrome (BSS), von Willebrand disease (vWD), Glanzmann's thrombasthenia or thrombocytopenia. Particularly, the method according to the present invention comprises the following procedural steps:
a) collection of blood sample
b) isolation of PRP (alternatively, whole blood can be used)
c) measuring of response of PRP sample to FC in comparison to a positive control (PRP from healthy donor) (aggregometer test) and data analysis.

The present invention will be now described, for illustrative but not limitative purposes, according to its preferred embodiments, with particular reference to its figures of the enclosed drawings.

FIG. 1 shows the chemical structure of FC

Figure 2:
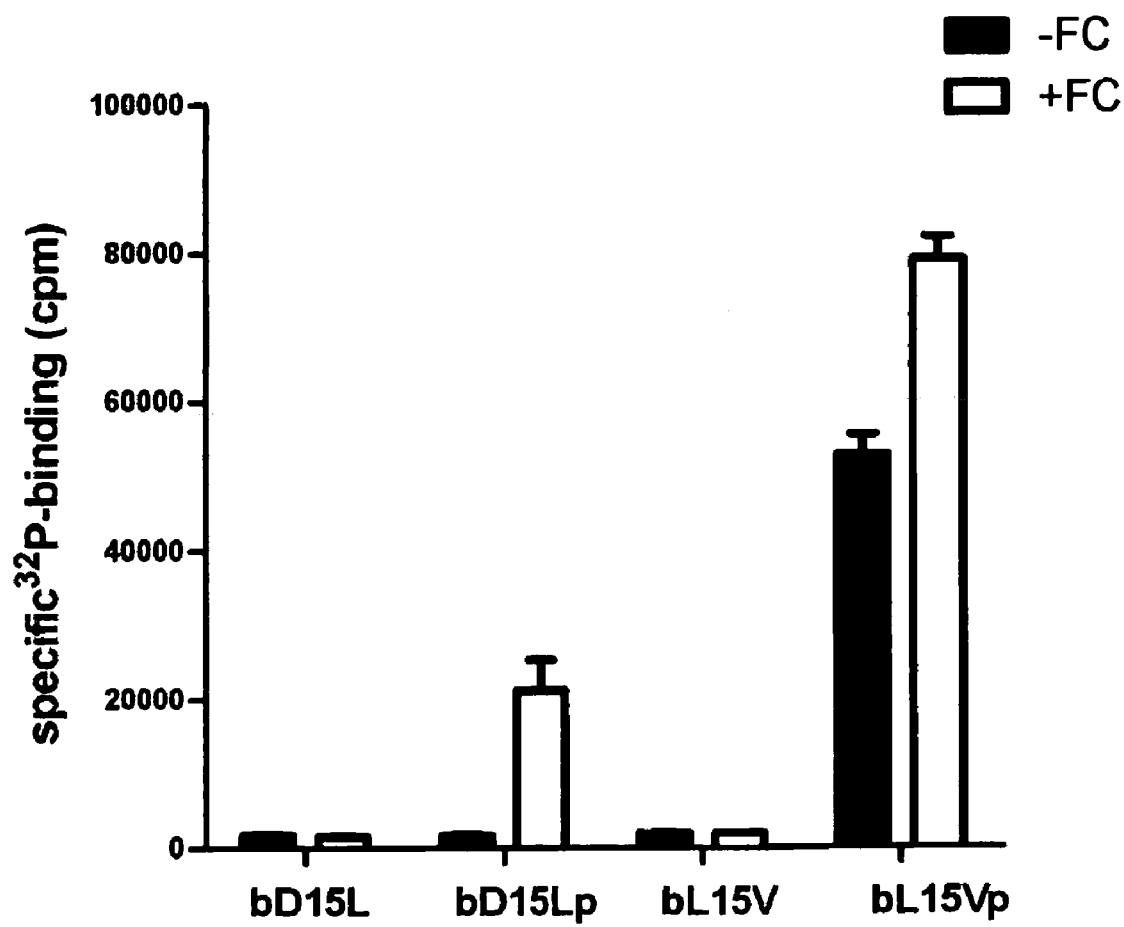

FIG. 2 shows the Effect of FC on 14-3-3 binding to immobilized bD15Lp and bL15Vp peptides. Peptides were immobilized onto streptavidin-agarose resin and incubated with $^{32}$P-labelled 14-3-3 in the absence or in the presence of 10 µM FC. After washing, radioactivity associated with the resin was measured. Data are the mean of three independent experiments.

Figure 3:
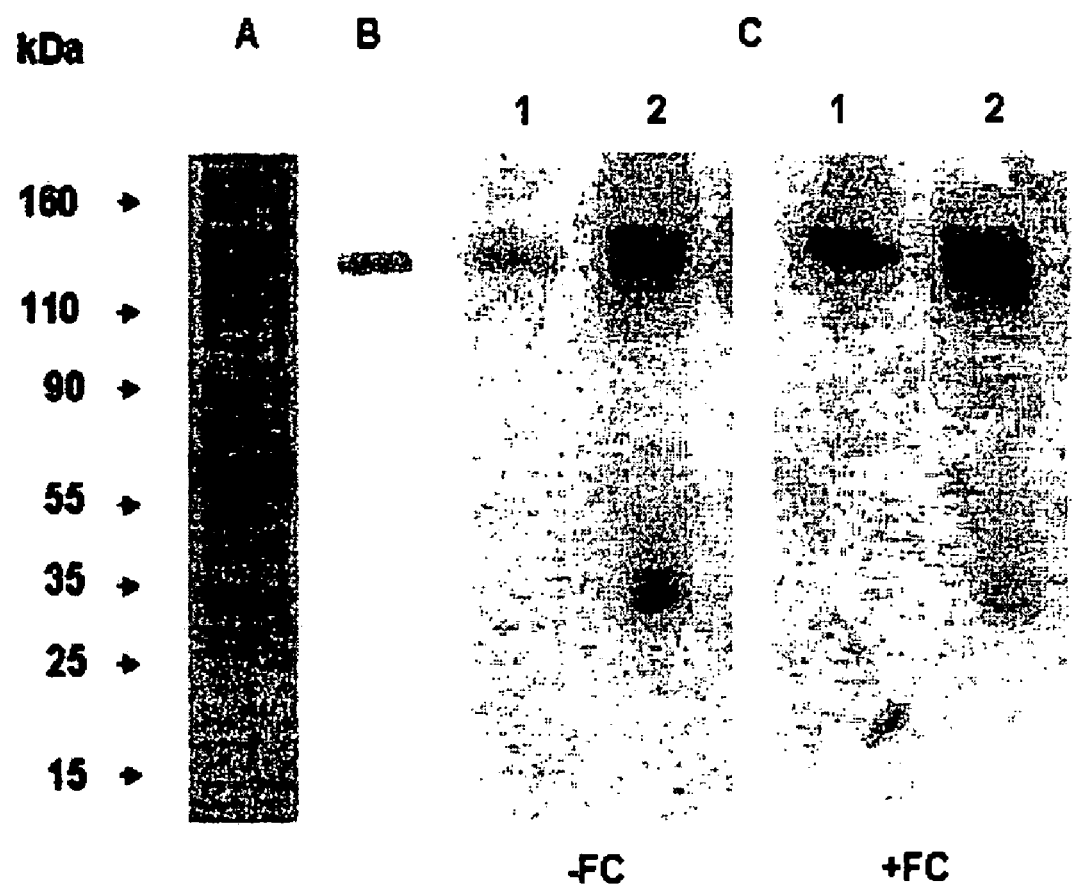

FIG. 3 shows the Effect of FC on the interaction between 14-3-3 proteins and GPIbα. A: SDS-PAGE profile of platelet proteins. B: immunodecoration of GPIbα with anti-GPIbα (CD24b) antidoby. C: overlay assay. Maize plasma membrane proteins (lanes 1, positive control) or platelet proteins (lanes 2) were separated by SDS-PAGE, blotted onto nitrocellulose membrane, incubated with $^{32}$P-14-3-3 in the absence (−FC) or in the presence (+FC) of 10 µM FC and subjected to autoradiography as described in the Materials and Methods.

Figure 4:
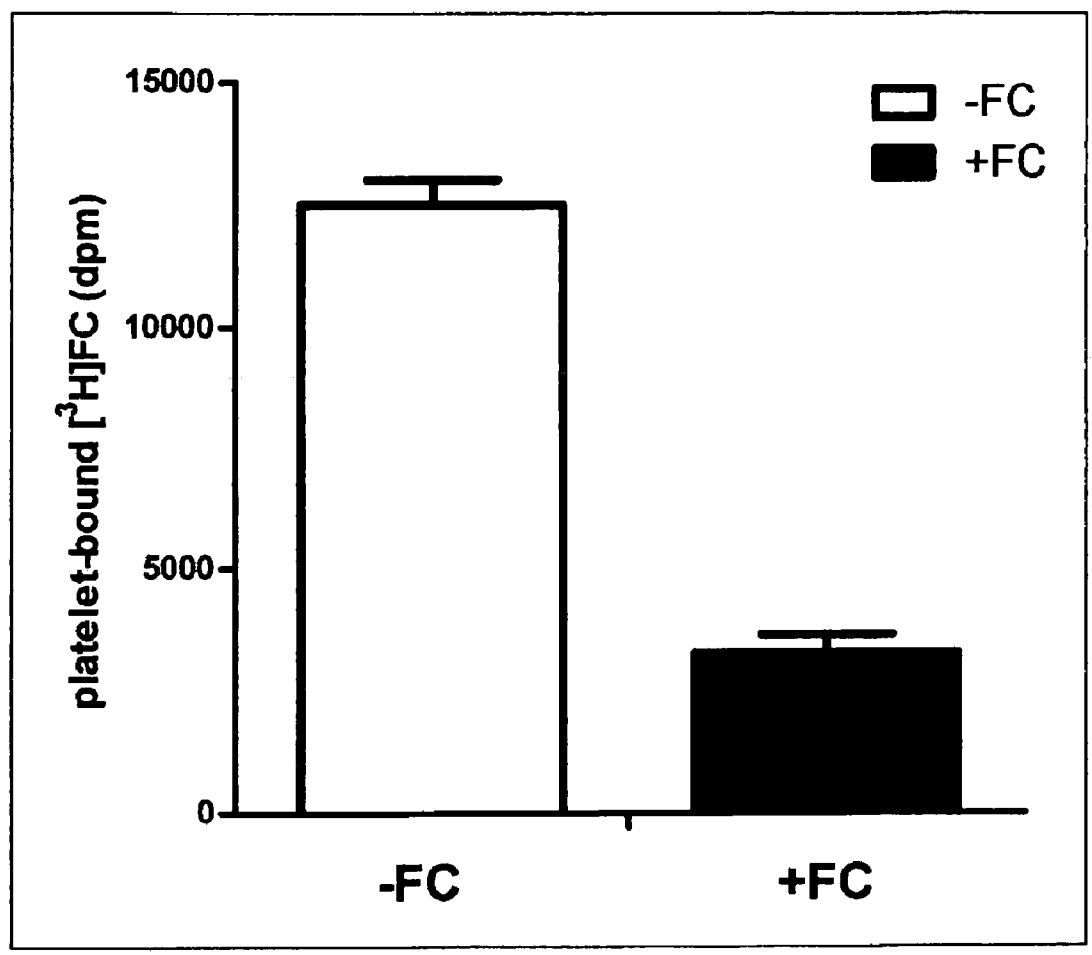

FIG. 4 shows the Binding of [$^{3}$H]FC to isolated human platelets. 30 µl of platelet suspension (2.0×10$^{8}$/ml) were incubated for 1 h at 37° C. with 5×10$^{5}$ dpm [$^{3}$H]FC in 100 µl PBS containing 5 mM MgCl$_2$. Where indicated, 10 µM cold FC was added (+FC). Platelets were then sedimented by centrifugation and radioactivity measured by scintillation counting.

Figure 5:
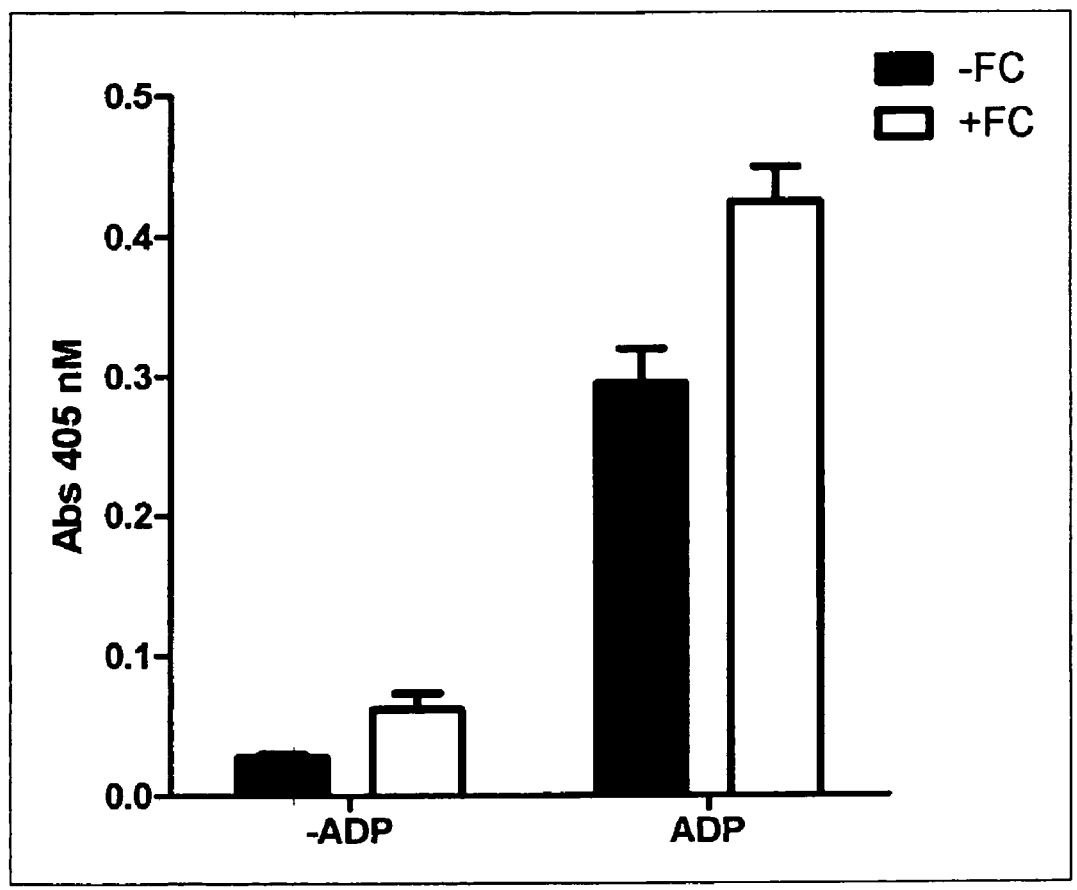

FIG. 5 shows the Effect of FC on platelet adhesion to immobilized vWF. 90 µl platelet suspension was incubated with purified vWF immobilized onto polystyrene wells. After washings, adherent platelets were determined measuring the endogenous acid phosphatase activity. +FC, platelets previously treated with 40 µM FC; +ADP, incubation in the presence of 50 µM ADP.

Figure 6:
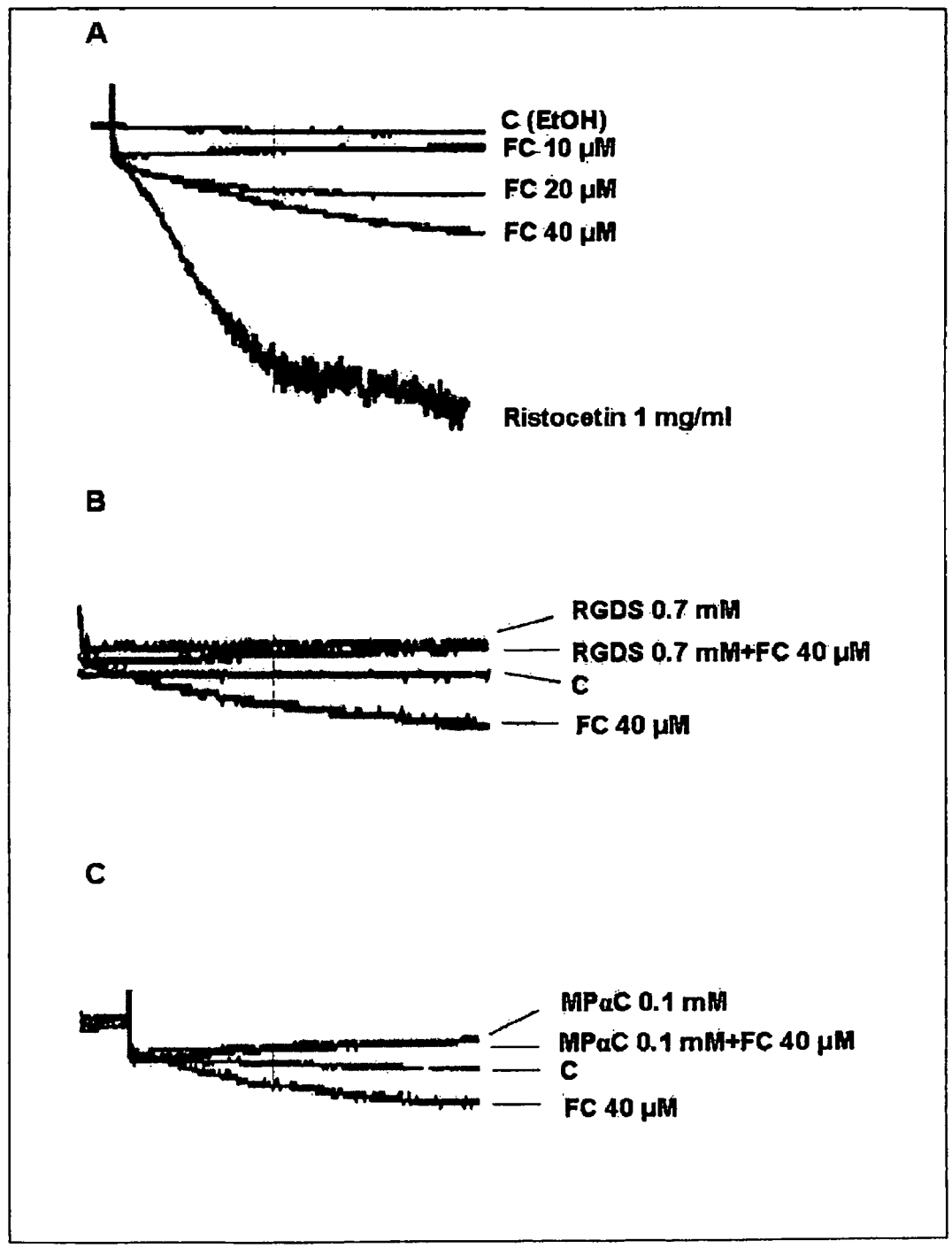

FIG. 6 shows the Effect of FC on platelet aggregation. Aggregation was studied with PRP using a turbidometric aggregometer as described in the Materials and Methods. A: effect of different concentrations of FC and ristocetin 1.0 mg/ml. B: effect of 40 µM FC in the presence of the aggregation antagonist RGDS peptide. C: effect of 40 µM FC in the presence of the cell-permeable 14-3-3 competitor MPαC peptide.

EXAMPLE 1

Study on Fusicoccin as Compound Able to Induce Platelet Aggregation

Materials and Methods

Chemicals

[γ$^{32}$P]ATP (specific activity 110 TBq/mmol) and thrombin were from Amersham Biosciences (Upssala, Sweden). FC was prepared according to Ballio et al. (1968). [$^{3}$H]FC, specific activity 63 Ci/mmol, was prepared as described by Ballio et al, (1980). Protein kinase A was from Sigma (St. Louis, Mo., USA). bD15L peptide (biotinyl-Asp-Leu-Leu-Ser-Thr-Val-Ser-Ile-Arg-Tyr-Ser-Gly-His-Ser-Leu), bD15Lp (biotinyl-Asp-Leu-Leu-Ser-Thr-Val-Ser-Ile-Arg-Tyr-Ser-Gly-His-pSer-Leu; pSer, phosphoserine), bL15V (biotinyl-Leu-Lys-Gly-Leu-Asp-Ile-Asp-Thr-Ile-Gln-Gln-Asn-Tyr-Thr-Val), and bL15Vp (biotinyl-Leu-Lys-Gly-Leu-Asp-Ile-Asp-Thr-Ile-Gln-Gln-Asn-Tyr-pThr-Val; pThr, phosphothreonine) were synthesized by Neosystem (Strasbourg, France). MPαC myristoylated peptide (C$_{13}$H$_{27}$CONH-Ser-Ile-Arg-Tyr-Ser-Gly-His-pSer-Leu) was synthesized by JPT Peptide Technologies (Berlin, Germany). Human von Willebrand Factor (Factor VIII Free) was purchased by Haematologic Technologies, Inc. (VT, USA). Anti-GPIbα (CD24b) antidoby was from Santa Cruz Biotechnology (CA, USA). Chemicals for gel electrophoresis were from Bio-Rad (CA, USA). RGDS peptide, ristocetin and the other chemicals were from Sigma-Aldrich (MI, USA).

Purification of Plasma Membrane from Maize Roots

Maize caryopses (*Zea mays* L. cv. Santos) from Dekalb (Mestre, Italy) were germinated and seedlings were grown in the dark for 5 days, as already described (Marra et al. 1996). Two-phase partitioned plasma membranes were obtained from 20 g of maize roots as previously described (Marra et al. 1996).

Expression in *Escherichia coli* of 14-3-3 Proteins

Recombinant GF14-6 was expressed in *E. coli* as fusion proteins with the glutathione-S-transferase (GST) using pGEX-2TK vector, following the procedure described by Fullone et al. (1998)

SDS-PAGE and Overlay Assay

SDS-PAGE was performed as described by Laemmli (1970), in a Mini Protean apparatus (Bio-Rad). The overlay assay was carried out according to Fullone et al. (1998), with minor modifications. The GST-fused 14-3-3 was labelled with [$\gamma^{32}$P]-ATP on cAMP-dependent protein kinase phosphorylation site present at junction between GST and the cloned protein, $^{32}$P-labelled GF14-6 was used as probe in the overlay experiments. 30 µl of platelet suspension ($2.0\times10^8$/ml) was boiled in Laemmli loading buffer, separated on SDS-PAGE and blotted on nitrocellulose membrane by semidry electroblotting. 20 µg of maize plasma membrane proteins were used as positive control. The membrane was blocked in buffer HT (25 mM Hepes-OH, 75 mM KCl, 5 mM MgCl$_2$, 1 mM DTT, 0.1 mM EDTA, 0.05% Tween 20, pH 7.5) containing 5% no-fat dried milk and then incubated overnight at 4° C. in buffer HT with 2% no-fat dried milk, 3 µg of $^{32}$P-labelled GF14-6 (8.3 kBq/ml). Where indicated, 10 µM FC was added. Nitrocellulose membrane was extensively washed with buffer HT and radioactivity detected by autoradiography.

Immunoblotting

For immunoblotting analysis, proteins separated by SDS-PAGE were electroblotted onto PVDF membrane with 39 mM glycine, 48 mM Tris, 0.1% SDS, 10% methanol. After blocking for 1 h in TTBS (20 mM Tris-HCl, 100 mM NaCl, 0.05% Tween 20, pH 7.5) with 5% no-fat dried milk at room temperature (RT), the membrane was incubated with the anti-GPIbα antibody (1:600). Following three washes with TTBS, the membrane was incubated with HRP-conjugated anti-rabbit (14-3-3) or anti-goat (GPIbα) secondary antibody.

Binding of GF14-6 to Resin-Bound Phosphopeptides 0.5 nmol of biotinylated peptides were immobilized onto 40 pl of streptavidin-agarose resin (Sigma-Aldrich) and incubated in 50 µl of buffer H with 3 µg of $^{32}$P-labelled GF14-6 (1.4 kBq/µg) for 60 min at room temperature in the absence or in the presence of 10 µM FC. Resin was then centrifuged at 2000×g for 5 min and washed three times with 1 ml of buffer H. Resin-bound radioactivity was measured in a liquid scintillation p-counter Packard Tri Carb 2100TR (Can berra, Australia).

Platelet Preparation

Washed platelets were prepared from platelet-rich plasma (PRP) obtained from healthy donors who had not taken medication for at least 9 days before bleeding. Preparation of PRP was performed as described by Dai et al. (2005).

FC Binding Activity of Platelets

30 µl of platelet suspension ($2.0\times10^5$/ml) were incubated for 1 h at 37° C. with $5\times10^5$ dpm [$^3$H]FC in 100 µl PBS containing 5 mM MgCl$_2$. To calculate specific binding, control sample was incubated with 10 µM FC. Platelets were centrifuged at 2000 g for 4 min in a refrigerated microcentrifuge and extensively washed in PBS containing 5 mM MgCl$_2$. 500 µl perchloric acid was then added and radioactivity was measured in a liquid scintillation β-counter.

Platelet Adhesion Assay

Platelet adhesion to immobilized vWF was performed in polystyrene microtitre plate wells as described by Lu et al. (1994) with minor modifications. Briefly, plate wells were coated overnight at 4° C. with 100 µl 15 µg/ml purified vWF and 15 µg/ml BSA. After three washes with PBS unbound sites were saturated with 200 µl of 2 mg/ml BSA for 2 h at RT. After three washings with PBS, wells were incubated with 90 µl platelet suspension ($2.0\times10^8$/ml) previously treated with 40 µM FC. Where indicated, wells were preloaded with 50 µM ADP. After 1 h incubation at RT, non-adherent platelets were removed by 7 washings with a buffer 10 mM Hepes containing 145 mM NaCl, 5 mM KCl, 1 mM MgCl$_2$, 2 mM CaCl$_2$, 10 mM glucose, 3.5 mg/ml BSA, pH 7.35. The number of vWF-bound platelet was calculated by measurement of endogenous acid phosphatase using 130 µl/well of developing buffer (10 mM p-nitrophenyl phosphate, 0.1% Triton X-100, 50 mM sodium citrate, pH 5.5). After 1 h at 37° C. incubation, the reaction was stopped by the addition of 10 pl of 1 M NaOH/well and the plates were read at 405 nm on an automated plate reader.

Platelet Aggregation

PRPs were preincubated at 37° C. with different FC concentrations and, when indicated 0.1 mM MPαC or 0.75 mM RGDS. Aggregation was measured using a turbidometric platelet aggregometer Chrono-log 560 CA (Chrono-log Corporation, PA, USA). 500 µl PRP were placed in a cuvette at 37° C. under continuous stirring at 1000 rpm. Aggregation was expressed as percentage of change in light transmission, with the value for the blank sample (PPP, Platelet-Poor Plasma) set at 100% and 0% for PRP.

Results

FC Promotes Binding of 14-3-3 Proteins to bD15Lp Peptide

A phosphorylated biotinyl-peptide (bD 15Lp), reproducing the last 15 amino acid residues of GPIbα, and containing the 14-3-3 binding sequence, was used in interaction studies with 14-3-3 proteins to verify the ability of FC to stimulate the interaction. The unphosphorylated corresponding peptide (bD15Lp) and peptides reproducing the last 15 amino acids of the HtATPase in unphosphorylated (bL15V) and phosphorylated form (bL15Vp) were used as control.

The peptides were immobilized onto a streptavidin-agarose resin and incubated with $^{32}$P-labelled 14-3-3 proteins. As shown in FIG. 2, the unphosphorylated peptides do not bind to 14-3-3 proteins, while the bL15Vp is able to interact with 14-3-3 and the interaction is strongly stimulated by FC. Interestingly, bD15Lp peptide is not able to associate to 14-3-3 proteins in the absence of FC, while in the presence of the toxin binding is generated.

This result demonstrates for the first time the ability of FC to promote the interaction between 14-3-3 proteins and a mode III binding motif different from the plant plasma membrane H$^+$-ATPase.

FC Stimulates the Interaction Between 14-3-3 Proteins and GPIbα

The interaction between 14-3-3 proteins and GPIbα was studied in vitro by means of an overlay assay. In this system $^{32}$P-labelled 14-3-3 proteins were used as probes and platelet proteins, separated by SDS-PAGE and then immobilized on nitrocellulose membrane, as baits. Autoradiography, reported in FIG. 3, shows that a band of 135 kDa, recognised by anti-GPIbα antibodies (lane B), is able to interact with $^{32}$P-labelled 14-3-3 proteins (lanes 2). Notably, the interaction is increased when 14-3-3 incubation was performed in the presence of 10 pM FC.

Purified Human Platelets Bind FC

In order to verify whether a FC binding activity is present in purified human platelets, a [$^3$H]FC analogue (Ballio et al., 1980) was utilised. 30 µl platelet suspension in PBS ($2.0\times10^8$/ml) were incubated with 10 nM [$^3$H]FC, and after several washings, the platelet-associated radioactivity was measured. The specific [$^3$H]FC binding was evaluated by adding a saturating concentration of unlabelled FC. As shown in FIG. 4, a relievable amount of [$^3$H]FC is associated to platelets. In the presence of 10 µM FC, radioactivity is significantly decreased, indicating that platelets possess specific FC binding activity.

FC Promotes Platelet Adhesion to vWF

The overlay experiment shown if FIG. 3 demonstrated that FC stimulates the association of 14-3-3 proteins to GPIbα. To investigate the physiological consequence of FC action, we studied its effect on the ability of platelets to adhere to vWF, which is the target of activated GPIbα. vWF was immobilized onto polystyrene microtitre plate wells and platelets were incubated in the presence of 50 µM of platelet agonist ADP and 10 µM FC. The number of adherent platelets was determined by measuring the endogenous acid phosphatase activity.

FIG. 5 shows the effect of pre-incubation of platelets with FC on their ability to bind vWF. The number of adherent platelets is significantly increased upon FC administration, either when resting platelets are used (−ADP) or in the presence of the platelet agonist ADP (+ADP). This finding suggests that FC is able to promote the GPIb-IX-V-mediated adhesion of platelet to purified vWF.

FC Triggers Platelet Aggregation

To determine whether the FC-promoted binding of platelets to vWF results in platelet aggregation, the effect of FC on platelet functionality was assayed using an optical aggregometer. As shown in FIG. 6A, FC induces a slight but reproducible agglutination in a dose-dependent manner, with a maximum at 40 µM FC. The effect does not resemble that of 1 mg/ml ristocetin, which brings about a rapid platelet agglutination. To determine whether the FC effect involves 14-3-3 proteins, the MPαC peptide was tested in FC-induced platelet agglutination. MPαC is a myristoylated cell-permeable peptide which reproduces the 1.4-3-3 binding sequence of GPIbα, and its ability to abolish 14-3-3-dependent platelet aggregation has been demonstrated.

As shown in FIG. 6B, MPαC completely inhibits FC effect, demonstrating that stabilization of GPIbα-14-3-3 interaction by FC is an essential step in FC-induced platelet agglutination. The effect of FC could be agglutination, a direct platelet-platelet interaction, resulting from cross-linking of platelets mediated by the binding of vWF to GPIb-IX-V complexes on adjacent platelets, or platelet aggregation. Aggregation is a more complex process that involves, besides binding of vWF to GPIb-IX-V, integrins activation and fibrinogen-mediated crosslinking of platelets.

The RGDS peptide reproduces amino acids 309-312 of the α-subunit of glycoprotein 0403 and inhibits platelet aggregation by competing with integrins for fibrinogen binding (Gartner et al., 1990). RGDS peptide completely blocks the aggregation induced by FC (FIG. 6C), demonstrating that its effect results in $\alpha_{IIB}\beta_2$ integrin activation and therefore triggers the aggregation process.

Discussion

FC exerts its toxic effects in plant causing a strong and permanent activation of the plasma membrane $H^+$-ATPase. In the last years, a large body of experimental evidence clarified the molecular mechanism of FC action (Aducci et al., 2002). FC promotes the interaction between the $H^+$-ATPase and regulatory 14-3-3 proteins, thus resulting in proton pump activation. Differently more 200 14-3-3 targets so far identified, the 14-3-3 binding site on the $H^+$-ATPase is located at the C-terminal end of the enzyme. This unusual binding motif has been defined as mode III.

Glycoprotein Ibα is a 14-3-3 target expressed in platelet plasma membrane. Since GPIbα shares with the plant $H^+$-ATPase a C-terminal mode III 14-3-3 binding site, we investigated whether FC could act on the 14-3-3/GPIbα interaction and could therefore regulate GPIbα function.

We demonstrated the ability of FC to bind to purified human platelets. Moreover, using a phosphopeptide reproducing the 14-3-3 binding site on GPIbα in an overlay assay, we showed that FC can stimulate 14-3-3 binding to GPIbα. FC binding results in GPIbα activation and consequent adhesion of platelets to vWF. Using a turbidometric aggregometer we also demonstrated that FC triggers the 14-3-3-dependent aggregation process.

Our data demonstrate that FC interfere with a critical step in hemostasis and suggest a possible use of the molecule in diagnosis and therapy of coagulation-correlated pathologies. In particular, Bernard-Soulier syndrome (BSS) and von Willebrand disease (vWD) are common hereditary coagulation abnormalities described in humans. They arise from a qualitative or quantitative deficiency of GPIbα or vWF, respectively (Pham and Wang, 2007; Sadler, 1994). Glanzmann's thrombasthenia, is a blood disorder in which platelets are defective in $\alpha_{IIB}\beta_2$ integrin (Seligsohn, 2002). Furthermore, a large number of bleeding pathologies lead to increased destruction or decreased production of platelets, hence resulting in thrombocytopenia (Kaushansky, 2008).

Diagnosis for these pathologies is currently made by measuring the ability of platelets to respond to exogenous modulators, such as ristocetin (De Luca et al., 2000) and botrocetin (Marsh, 2001). The bacterial glycopeptide ristocetin and the snake venom toxin botrocetin modulate vWF to elicit platelet glycoprotein 1b binding activity and lead to platelet agglutination (De Luca et al., 2000; Marsh, 2001). PRP from patients affected by BSS or vWD shows an abnormal response to these molecules.

The dramatic effects on platelet aggregation induced by ristocetin and botrocetin made them unsuitable for therapy. The elected therapy for BSS is currently based on blood or platelets transfusion, while vWD is commonly treated with human derived medium purity factor VIII concentrates complexed to vWF.

On the contrary, FC induces a mild platelet aggregation by a different molecular mechanism in a dose-dependent manner. This renders feasible the use of FC in diagnosis and therapy of bleeding disorders.

Finally, structure-activity relationships studies will be useful for the design of FC analogues with an increased ability to stimulate the association between GPIbα and 14-3-3 proteins. Alternatively, natural compounds structurally related to FC, such as ophyobolins and cotylenins (Aducci at al., 2003), could also be assayed.

Recently, a number of 14-3-3 ligands characterized by mode III binding sequences have been identified (Coblitz et al., 2006). Since our finding demonstrates the ability of FC to stabilize the interaction between 14-3-3 and a target with C-terminal motif, it is conceivable that FC mode of action can be extended in other biological processes.

REFERENCES

Aducci, P., Camoni L., Fullone, M. R., and Visconti, S. (2003). "Fusicoccin: Phytotoxin or molecular signal?" In "Bacterial, Plant & Animal Toxins". Ascenzi P., Polticelli F. and Visca P. eds., Research Signpost, Trivandrum, India.

Aducci, P., Camoni, L., Marra, M. and Visconti, S. (2002). From cytosol to organelles: 14-3-3 proteins as multifunctional regulators of plant cell. IUBMB Life 53, 49-55.

Andrews, R. K., Harris, S. J., McNally, T., and Berndt, M. C. (1998). Binding of purified 14-3-3 zeta signaling protein to discrete amino acid sequences within the cytoplasmic domain of the platelet membrane glycoprotein 1b-IX-V complex. Biochemistry 37, 638-647

Ballio, A., Carilli, A., Santurbano, B., and Tuttobello, L. (1968). Pilot plant production of fusicoccin. Ann. 1st. Sup. San. 4, 317-332.

Ballio, A., Federico, R., Pessi, A., and Scalorbi, D. (1980). Fusicoccin binding sites in subcellular preparations of spinach leaves. Plant Sci. Lett. 18, 39-44.

Coblitz, B., Wu, M., Shikano, S., and Li, M. (2006). C-terminal binding: An expanded repertoire and function of 14-3-3 proteins. FEBS Lett. 580, 1531-1535.

Dai, K., Bodnar, R., Berndt, M. C., and Du, X. (2005). A critical role for 14-3-3 protein in regulating the VWF binding function of platelet glycoprotein 1b-IX and its therapeutic implications. Blood 106, 1975-1981.

De Luca, M., Facey, D. A., Favaloro, E. J., Hertzberg, M. S., Whisstock, J. C., McNally, T., Andrews, R. K., and Berndt, M. C. (2000). Structure and function of the von Willebrand factor A1 domain: analysis with monoclonal antibodies reveals distinct binding sites involved in recognition of the platelet membrane glycoprotein 1b-IX-V complex and ristocetin-dependent activation. Blood. 95, 164-172.

Du, X., Fox, J. E., and Pei, S. (1996). Identification of a binding sequence for the 14-3-3 protein within the cytoplasmic domain of the adhesion receptor, platelet glycoprotein Ibα. J. Biol. Chem. 271, 7362-7367.

Fu, H., Subramanian, R. R., and Masters, S. C. (2000). 14-3-3s: structure function and regulation. Annu. Rev. Pharmacol. Toxicol. 40, 617-647.

Fullone, M. R., Visconti, S., Marra, M., Fogliano, V., and Aducci, P. (1998). Fusicoccin effect on the in vitro interaction between plant 14-3-3 proteins and plasma membrane 1-1+-ATPase. J. Biol. Chem. 273, 7698-7702.

Furie, B., and Furie, B. C. (1988). The molecular basis of blood coagulation. Cell. 20, 505-518.

Gartner, T. K., and Taylor, D. B. (1990). The amino acid sequence Gly-Ala-Pro-Leu appears to be a fibrinogen binding site in the platelet integrin, glycoprotein I1b. Thromb Res. 60, 291-309.

Gralnick, H. R., Williams, S. B., and Coller, B. S. (1985). Asialo von Willebrand factor interactions with platelets: interdependence of glycoproteins 1b and I1b/IIIa for binding and aggregation. J. Olin. Invest. 75, 19-25.

Graniti, A., Ballio, A., and Marre, E. (1994). Phatogenesis and host specificity in plant diseases. Sing, U. S., Kohomoto, K., and Singh, R. P. (Eds), Elsevier, Oxford, 103

Kaushansky, K. (2008). Historical review: megakaryopoiesis and thrombopoiesis. Blood. 111, 981-986.

Laemmli, U. K. (1970). Cleavage of the structural proteins during the assembly of the head of the bacteriofage T4. Nature 277, 680-685.

Lu, X., Williams, J. A., Deadman J. J., Salmon G. P., Kakkar V. V., Wilkinson J. M., Baruch D., Authi K. S., and Rahman S. (1994). Preferential antagonism of the interactions of the integrin alpha I1b beta 3 with immobilized glycoprotein ligands by snake-venom RGD (Arg-Gly-Asp) proteins. Evidence supporting a functional role for the amino acid residues flanking the tripeptide RGD in determining the inhibitory properties of snake-venom RGD proteins. Biochem J. 304, 929-936.

Marra, M., Fogliano V., Zambardi, A., Fullone, M. R., Nasta, D., and Aducci, P. (1996). The H+-ATPase purified from maize root plasma membranes retains fusicoccin in vivo activation. FEBS Lett. 382, 293-296.

Marre, E. (1979). Fusicoccin: a tool in plant physiology. Ann. Rev. Plant Physiol 30, 273-288. Marsh, N. A. (2001). Diagnostic uses of snake venom. Haemostasis 31, 211-217.

Muslin, A. J., Tanner, J. W., Allen, P. M., and Shaw, A. S. (1996). Interaction of 14-3-3 with signaling proteins is mediated by the recognition of phosphoserine. Cell 84, 889-897.

Pham, A., and Wang, J. (2007). Bernard-Soulier syndrome: an inherited platelet disorder. Arch Pathol Lab Med. 131, 1834-1836.

Sadler, J., E. (1994). A revised classification of von Willebrand disease. For the Subcommittee on von Willebrand Factor of the Scientific and Standardization Committee of the International Society on Thrombosis and Haemostasis. Thromb Haemost. 71, 520-525.

Seligsohn, U. (2002). Glanzmann thrombasthenia: a model disease which paved the way to powerful therapeutic agents. Pathophysiol. Haemost. Thromb. 32, 216-217.

Yaffe, M. B., Rittinger, K., Volinia, S., Caron, P. R., Aitken, A., Leffers, H., Gamblin, S. J., Smerdon, S. J., and Cantley, L. C. (1997). The structural basis for 14-3-3: phosphopeptide binding specificity. Cell 91, 961-971.

Ware, J. (1998). Molecular analyses of the platelet glycoprotein 1b-IX-V receptor. Thromb Haemost. 79, 466-478.

The invention claimed is:

1. A method for treating coagulation-correlated pathologies comprising administering a therapeutically effective amount of at least one tricyclic terpenes chosen from the group consisting of fusicoccin, ophyobolins or cotylenins to a subject in need of such treatment.

2. The method according to claim 1, wherein the coagulation-correlated pathologies are chosen from the group consisting of Bernard-Soulier syndrome, (BSS), von Willebrand disease (vWD), Glanzmann's thrombasthenia or thrombocytopenia.

3. A method for diagnosing coagulation-correlated pathologies comprising contacting a sample with at least one tricyclic terpenes chosen from the group consisting of fusicoccin, ophyobolins or cotylenins in vitro.

4. The method according to claim 3, wherein the coagulation-correlated pathologies are chosen from the group consisting of Bernard-Soulier syndrome (BSS), von Willebrand disease (vWD), Glanzmann's thrombasthenia or thrombocytopenia.

5. The method according to claim 4 comprising the following procedural steps:
   a) collection of blood sample;
   b) optionally, isolation of PRP;
   c) measuring the response of PRP sample to FC in comparison with positive control and data analysis.

* * * * *